US011478217B2

(12) United States Patent
Bautista et al.

(10) Patent No.: US 11,478,217 B2
(45) Date of Patent: Oct. 25, 2022

(54) CATHETER EXTENSION

(71) Applicant: ACIST Medical Systems, Inc., Eden Prairie, MN (US)

(72) Inventors: Richard A. Bautista, Palo Alto, CA (US); David Johnson, Menlo Park, CA (US); Isaac Kim, San Jose, CA (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 938 days.

(21) Appl. No.: 16/235,153

(22) Filed: Dec. 28, 2018

(65) Prior Publication Data
US 2019/0200952 A1 Jul. 4, 2019

Related U.S. Application Data

(60) Provisional application No. 62/611,729, filed on Dec. 29, 2017.

(51) Int. Cl.
*A61B 8/00* (2006.01)
*A61M 25/00* (2006.01)
*A61M 39/12* (2006.01)
*A61B 8/12* (2006.01)

(52) U.S. Cl.
CPC ............ *A61B 8/12* (2013.01); *A61B 8/445* (2013.01); *A61M 25/0014* (2013.01); *A61M 39/12* (2013.01)

(58) Field of Classification Search
None
See application file for complete search history.

(56) References Cited

U.S. PATENT DOCUMENTS

2013/0281851 A1* 10/2013 Carr .................. A61B 18/1815
600/435
2014/0343434 A1* 11/2014 Elbert ...................... A61B 8/12
600/467
2016/0143616 A1* 5/2016 Okubo ................. A61M 39/10
600/467

FOREIGN PATENT DOCUMENTS

JP            3331136 B2    10/2002
JP         2011067537 A     4/2011

OTHER PUBLICATIONS

International Patent Application No. PCT/US2018/067839, International Search Report and Written Opinion dated Mar. 1, 2019, 12 pages.

* cited by examiner

*Primary Examiner* — Shahdeep Mohammed
(74) *Attorney, Agent, or Firm* — Fredrikson & Byron, P.A.

(57) ABSTRACT

A catheter extension can include an extension body with a sheath defining a lumen, a cable extending within the lumen, a proximal connector attached to the sheath and configured to couple to a catheter drive mechanism, and a distal connector attached to the sheath and configured to couple to a catheter. An axial biasing member can be coupled to the cable and integrated into either the proximal or distal connector and configured to exert a force on the cable in a first axial direction and permit movement of the cable in a second axial direction. An axial key can be coupled to the cable and integrated into the connector opposite the axial biasing member. The axial key can include a tab attached to the cable and a slot with an inner profile that complements a tab outer profile that can permit the tab to move in within the slot.

17 Claims, 17 Drawing Sheets

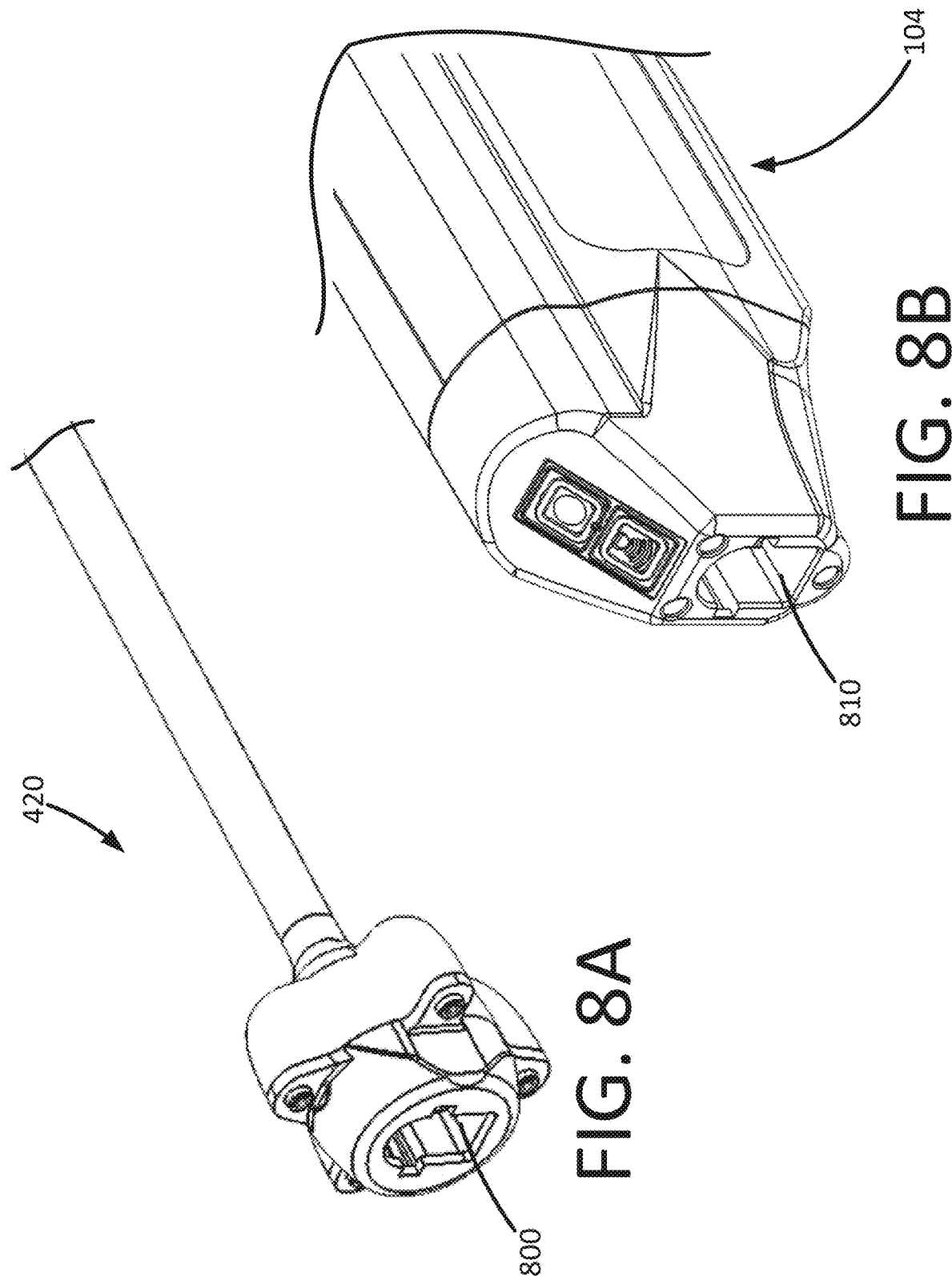

CATHETER EXTENSION

RELATED APPLICATIONS

This application claims priority to U.S. Provisional Patent Application No. 62/611,729, filed Dec. 29, 2017, the entire contents of which is incorporated herein by reference.

TECHNICAL FIELD

This disclosure generally relates to extending catheter assemblies.

BACKGROUND

Medical imaging techniques generally can be used to collect data and generate in-vivo visualization of anatomical areas of interest. One such example is intravascular imaging, where vascular structures and lumens may be imaged. For instance, intravascular imaging may be used to produce one or more images of the coronary artery lumen, coronary artery wall morphology, and devices, such as stents, at or near the coronary artery wall. Images generated using medical imaging techniques can be useful for diagnostic purposes, such as identifying diagnostically significant characteristics of a vessel.

To collect image data, intravascular imaging procedures generally use an imaging probe positioned within a catheter that is inserted within a vascular structure. However, before image data can be collected steps are usually taken to prepare the catheter for use. Equipment used in medical operations is sterilized to reduce the risk of infection. One-time-use medical devices, such as catheters, can be packaged sterile and opened in a sterile environment.

However, catheters in particular typically require additional equipment to operate. This operating equipment can become contaminated, especially if it is a multiple use device. Sterile barriers have been used traditionally used to cover the additional operating equipment and maintain a sterile operating environment. Yet, with this arrangement, the user must manipulate and operate the additional equipment through the sterile barrier, which can be cumbersome.

SUMMARY

This disclosure provides a catheter extension that separates a catheter from other operating equipment at a distance that maintains a sterile operating environment. Embodiments generally comprise a catheter extension that includes an extension body, a proximal connector, a distal connecter, an axial biasing member, and an axial key. The extension body can have a proximal end and a distal end and include a sheath that defines a lumen. A cable can extend within the lumen. The proximal connector can be attached to the sheath at the proximal end of the extension body and can be configured to be coupled to a catheter drive mechanism. The distal connector can be attached to the sheath at the distal end of the extension body and can be configured to be coupled to a catheter.

The axial biasing member can be coupled to the cable and integrated into either the proximal connector or the distal connector. As assembled, the axial biasing member can be configured to exert a force on the cable in a first axial direction to facilitate connection between the cable and either the catheter drive mechanism or the catheter. The axial biasing member can permit movement of the cable in a second axial direction. The second axial direction can be opposite of the first axial direction.

The axial key can be coupled to the cable. The axial key can be integrated into whichever of the proximal connector and the distal connector is not coupled to the axial biasing member. The axial key can include a tab and a slot. The tab can be attached to the cable and can have an outer profile. The slot can have an inner profile that complements the outer profile of the tab. The slot can permit the tab to move in the second axial direction within the slot.

In setup, the user can couple the proximal connector of the catheter extension to a catheter drive mechanism and the distal connector of the catheter extension to a catheter. When the components are coupled, the axial biasing member to can facilitate connection between the cable and either the catheter drive mechanism or the catheter and permit movement of the cable. When assembled, the tab can move in an axial direction within the slot.

In use, the user can utilize the catheter extension to conduct an operation. The operation can involve communicating electrically between the catheter drive mechanism and the catheter through the catheter extension and rotating the catheter with the catheter drive mechanism through the catheter extension.

The catheter extension allows for operation without having to cover the catheter drive mechanism with a sterile barrier. Traditionally, users would cover, manipulate, and operate the catheter drive mechanism with a sterile barrier. The catheter was connected to the catheter drive mechanism through an opening in the sterile barrier. Interacting and manipulating the catheter drive mechanism through a sterile barrier can be cumbersome. In addition, installing the sterile barrier can require multiple users and a significant amount of time. The present disclosure allows for operation without a sterile barrier. The length of the catheter extension allows the sterile catheter to be sufficiently isolated from the non-sterile catheter drive mechanism. Thus, the catheter remains sterile when it is plugged into the extension, as the extension itself is sterilized prior to use.

The details of one or more examples are set forth in the accompanying drawings and the description below. Other features, objects, and advantages will be apparent from the description and drawings.

BRIEF DESCRIPTION OF DRAWINGS

The following drawings are illustrative of particular embodiments of the present invention and therefore do not limit the scope of the invention. The drawings are not necessarily to scale (unless so stated) and are intended for use in conjunction with the explanations in the following description. Embodiments of the invention will hereinafter be described in conjunction with the appended drawings, wherein like numerals denote like elements.

FIG. 8A is a perspective view of the catheter extension distal connector.

FIG. 8B is a perspective view of the catheter drive mechanism.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Figure 1:
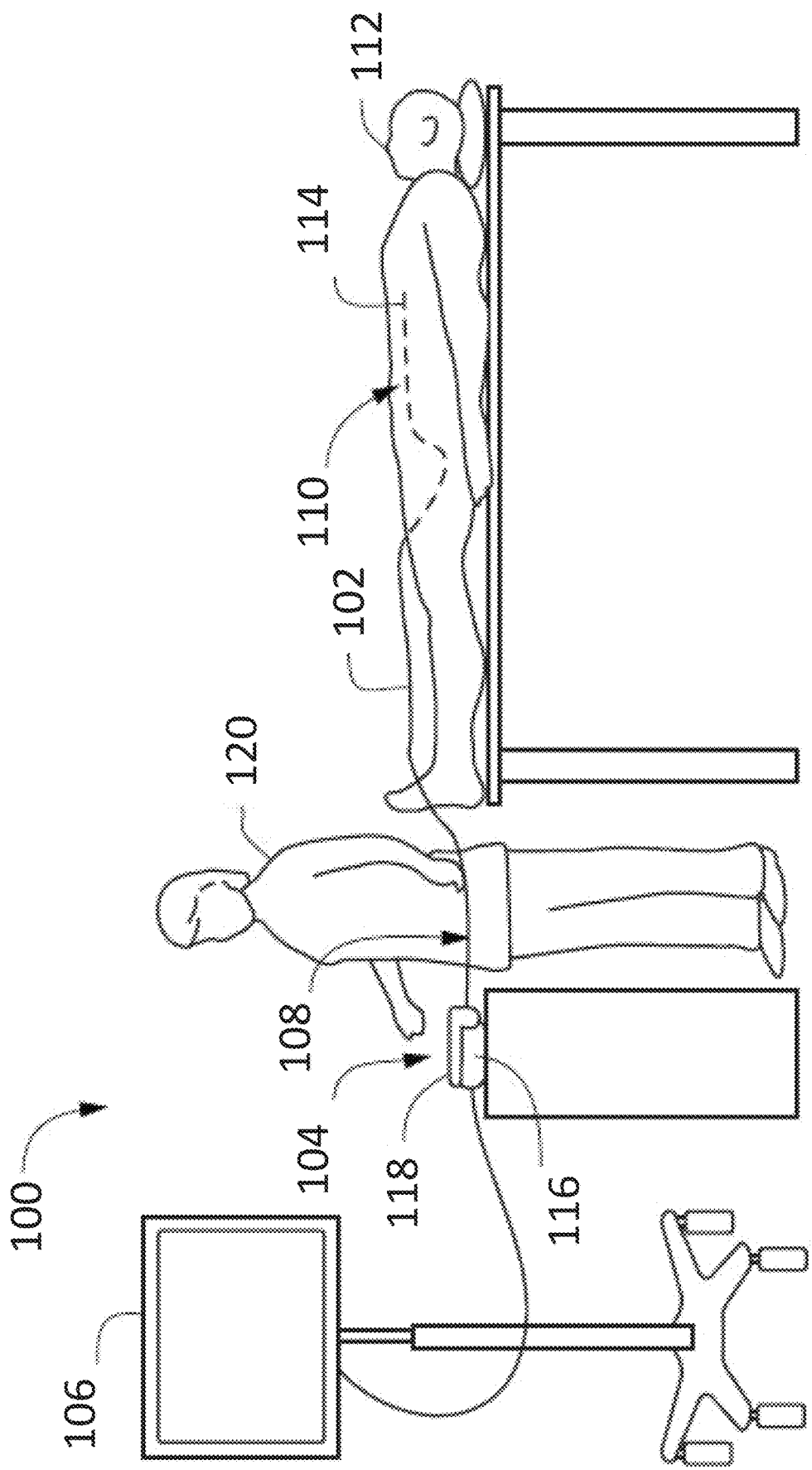
FIG. 1 is an example of a system configured to perform intravascular imaging.

FIG. 1 illustrates an example of a system 100 that may be configured to perform intravascular imaging. System 100 can include a catheter 102, a catheter drive mechanism 104, and an imaging engine 106. The catheter 102 may include a proximal end 108 and a distal end 110 configured to be inserted into a vessel of a patient 112. In one example, catheter 102 may be inserted into the patient 112 via the femoral artery and guided to an area of interest within the patient 112. The broken lines in FIG. 1 represent portions of catheter 102 within the patient 112.

In some examples, the catheter 102 can include an intravascular imaging device 114 configured to generate image data. Intravascular imaging device 114 can be in communication with imaging engine 106. In some embodiments, intravascular imaging device 114 is an ultrasound transducer configured to emit and receive ultrasound energy and generate ultrasound imaging data. The image data generated by the imaging device 114 can represent a cross-section of an area of interest within the patient 112 at the location of the imaging device 114. The image data generally will represent a plurality of image items at the cross-sectional location of the imaging device 114, such as, for example, various layers of a vessel of the patient 112 and/or any accumulated matter within the vessel (e.g., plaque).

The catheter drive mechanism 104 can be configured to translate intravascular imaging device 114 of catheter 102. The catheter drive mechanism 104 may comprise a linear translation system (LTS) 116. The LTS 116 may be mechanically engaged with catheter 102 and configured to translate catheter 102 a controlled distance within the patient 112 during a translation operation, for example a pullback or push-forward operation. The catheter drive mechanism 104 may comprise a patient interface module (PIM) 118 configured to interface the catheter drive mechanism 104 with the catheter 102. Translating the imaging device 114 can allow for cross-sectional image data to be collected at various longitudinal locations within a vessel of the patient 112. This cross-sectional image data at various longitudinal locations can then be compiled, in some applications, to generate a longitudinal cross-sectional image of an area of interest.

The imaging engine 106 can be in communication with intravascular imaging device 114 and/or catheter drive mechanism 104. According to some examples, the imaging engine 106 may comprise at least one programmable processor. In some examples, the imaging engine 106 may comprise a computing machine including one or more processors configured to receive commands from a system user 120 and/or display data acquired from catheter 102 via a user interface thereof. The computing machine may include computer peripherals (e.g., keyboard, mouse, electronic display) to receive inputs from the system user 120 and output system information and/or signals received from catheter 102 (e.g., rendered images). In some examples, the user interface of the computing machine may be a touchscreen display configured to act as both an input device and an output device. In some examples, imaging engine 106 may include memory modules for storing instructions, or software, executable by the one or more processors.

Figure 2:
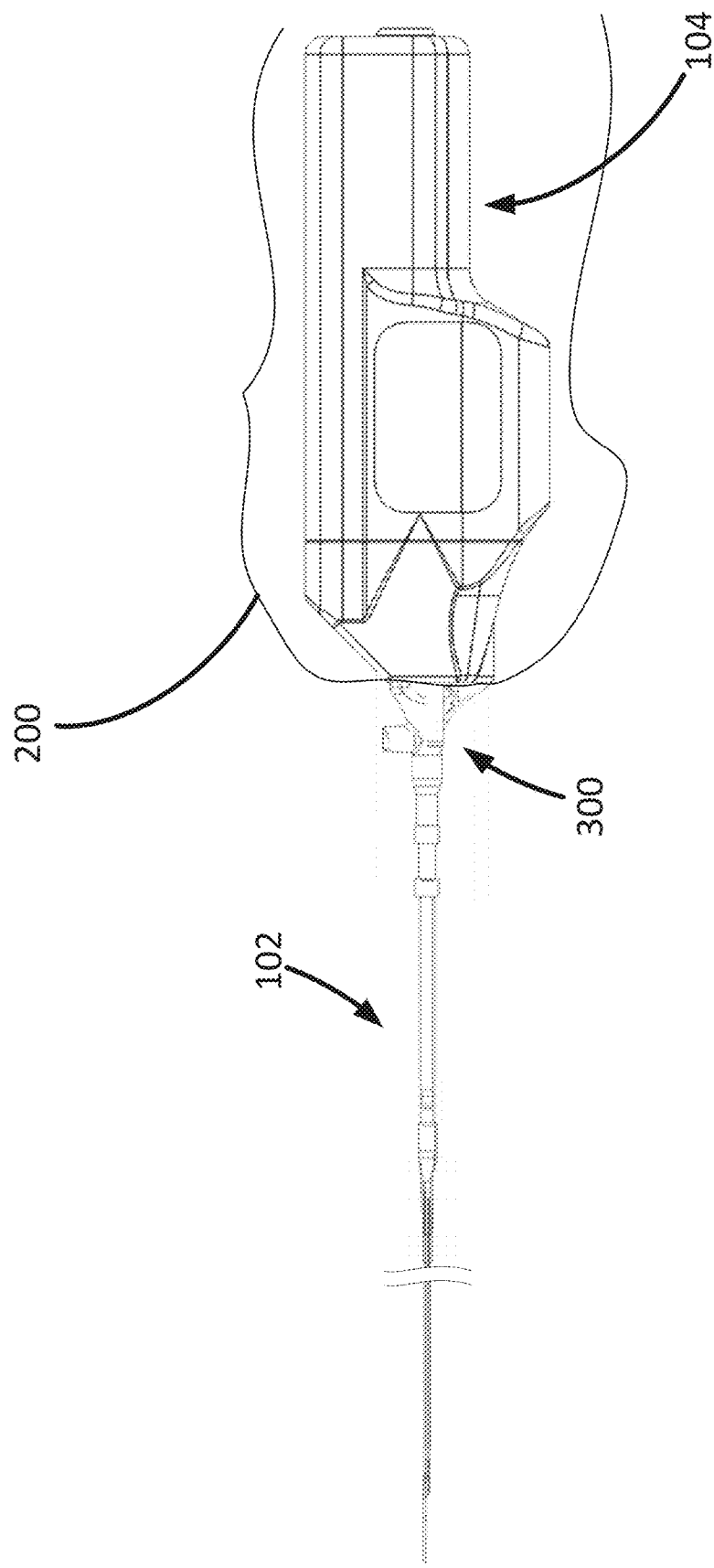
FIG. 2 is a schematic, side elevational view of an intravascular imaging system.

FIG. 2 provides a closer view of a catheter 102 coupled to a catheter drive mechanism 104, with a sterile barrier 200 covering the catheter drive mechanism 104. To provide a sanitary operating environment, the catheter drive mechanism 104 is typically covered in a sterile barrier 200. An opening in the sterile barrier 200 at the face of the catheter drive mechanism 104 allows the proximal hub 300 of the catheter 102 to pass through and plug into the catheter drive mechanism 104. The sterile barrier 200 helps to prevent contamination of the catheter 102 by the catheter drive mechanism 104. The sterile barrier 200 can extend to the length of catheter drive mechanism 104 plus any power lines.

Installing the sterile barrier 200 can require two or more individuals. One sterile individual can hold the bag while the non-sterile individual inserts the catheter drive mechanism 104 into the bag. Then the non-sterile individual can pull the end of the sterile barrier 200 to the end of the farthest point in of the catheter drive mechanism 104. The sterile barrier 200 can be made of transparent, pliable material to enable the user to see and operate the catheter drive mechanism 104.

The components of a conventional intravascular imaging system can be coupled together as illustrated in FIGS. 3A-3E. The proximal hub 300 of the catheter 102 can be configured to be mechanically coupled to the catheter drive mechanism 104 using a proximal hub 300. Components of the catheter drive mechanism 104 can mate with corresponding components of the proximal hub 300 of the catheter 102. The mating components of the catheter 102 and catheter drive mechanism 104 can be configured to rotate components of the catheter 102 after they are coupled.

Figure 3A:
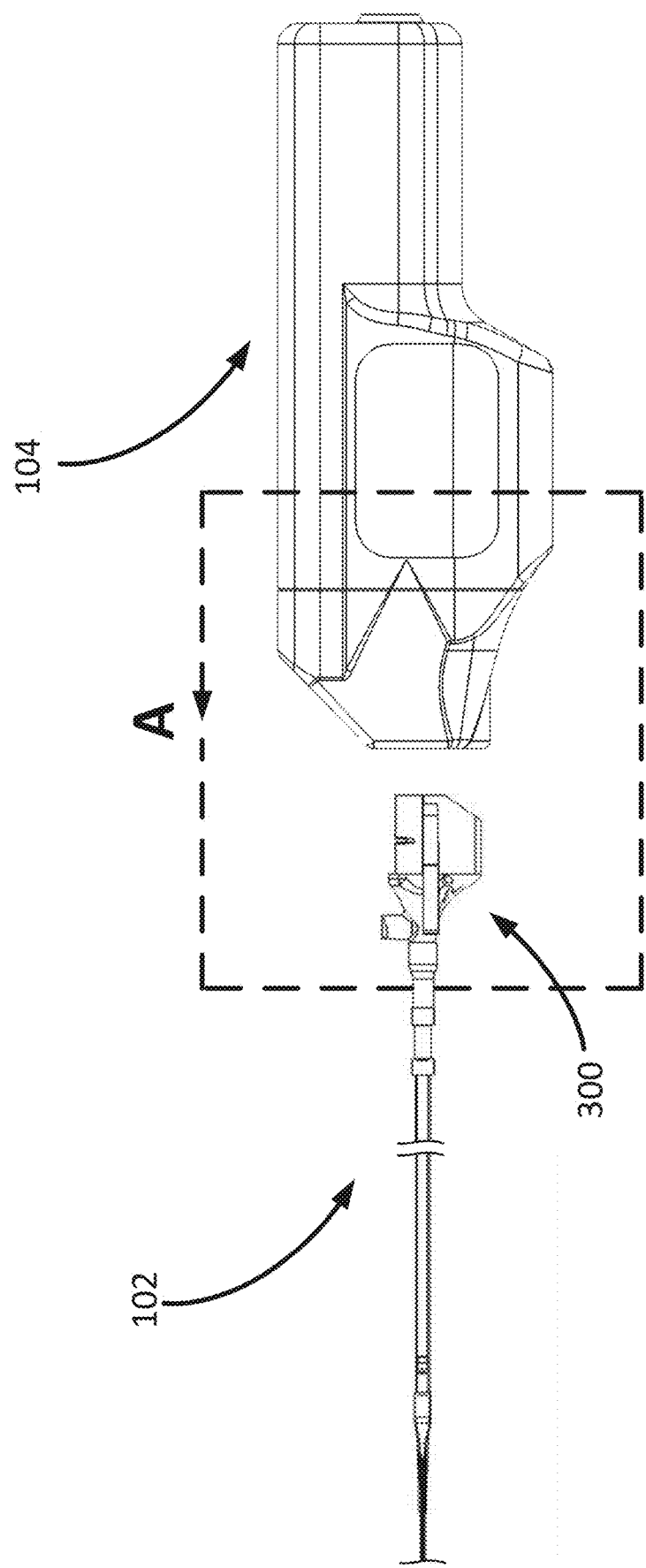
FIG. 3A is a side elevational view of a catheter just before connecting to a catheter drive mechanism.

FIG. 3A shows the catheter 102 and the catheter drive mechanism 104 just before they are coupled together. The catheter drive mechanism 104 can have a connection port configured to receive the proximal hub 300 of the catheter 102. As the catheter 102 and the catheter drive mechanism 104 are coupled, components of the catheter 102 can be moved. The user can press the proximal hub 300 into the catheter drive mechanism 104 connection port. As the proximal hub 300 of the catheter 102 is coupled, components of the proximal hub 300 can become compressed.

Figure 3B:
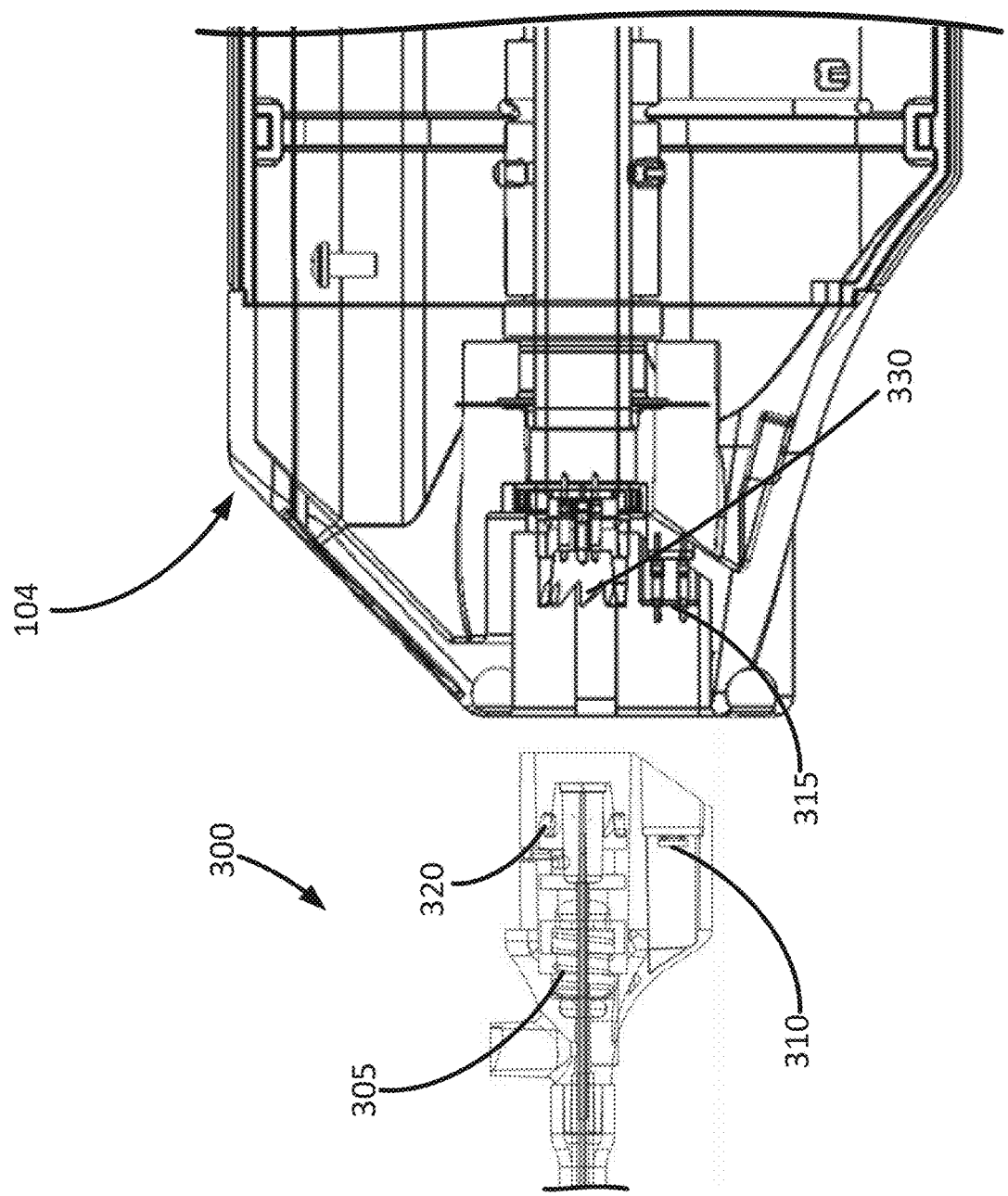
FIG. 3B is a mid-plane cross-sectional view of section A from FIG. 3A.

FIG. 3B illustrates a closer view of the connection between the catheter 102 and the catheter drive mechanism 104. The catheter drive mechanism 104 can have circumferential teeth 330 connected to a drive mechanism. The proximal hub 300 can have corresponding circumferential teeth 320 that mate with those of the catheter drive mechanism 104. The proximal hub 300 can have an axial biasing member 305 that moves when the catheter 102 and the catheter drive mechanism 104 are coupled. The proximal hub 300 can have one or more electrical connections 310 that mate with corresponding electrical connections 315 in the catheter drive mechanism 104. The electrical connections 310, 315 can allow for electrical communication between the catheter 102 and the catheter drive mechanism 104.

Figure 3C:
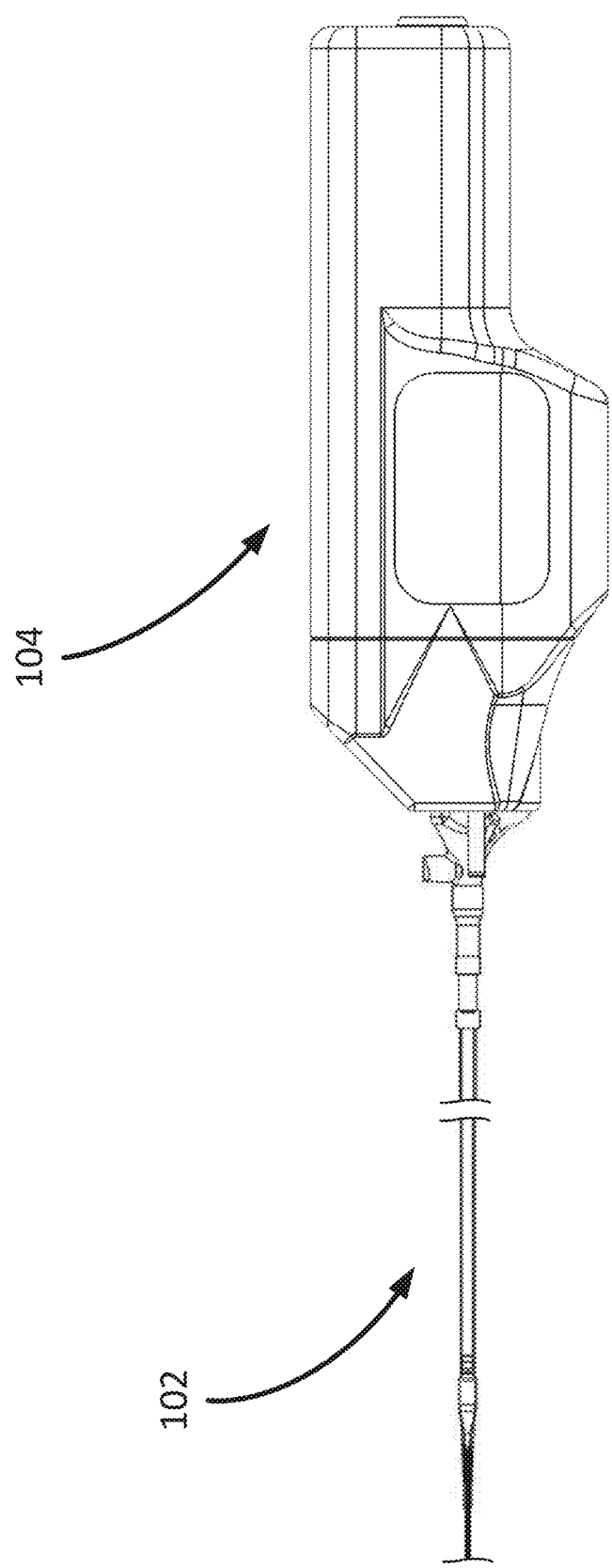
FIG. 3C is a side elevational view of a catheter after connecting to a catheter drive mechanism.

FIG. 3C shows the catheter drive mechanism 104 and the catheter 102 when coupled together. An axial biasing member (305 in FIG. 3B) can be compressed as the catheter 102 and the catheter drive mechanism 104 are coupled. At this point, the circumferential teeth (320 in FIG. 3B) of the catheter 102 can be mated to circumferential teeth (330 in FIG. 3B) the catheter drive mechanism 104 such that the catheter drive mechanism 104 can rotate components of the catheter 102. The electrical connections (310, 315 in FIG. 3B) can provide electrical transfer after the catheter 102 and the catheter drive mechanism 104 are coupled.

Figure 3D:
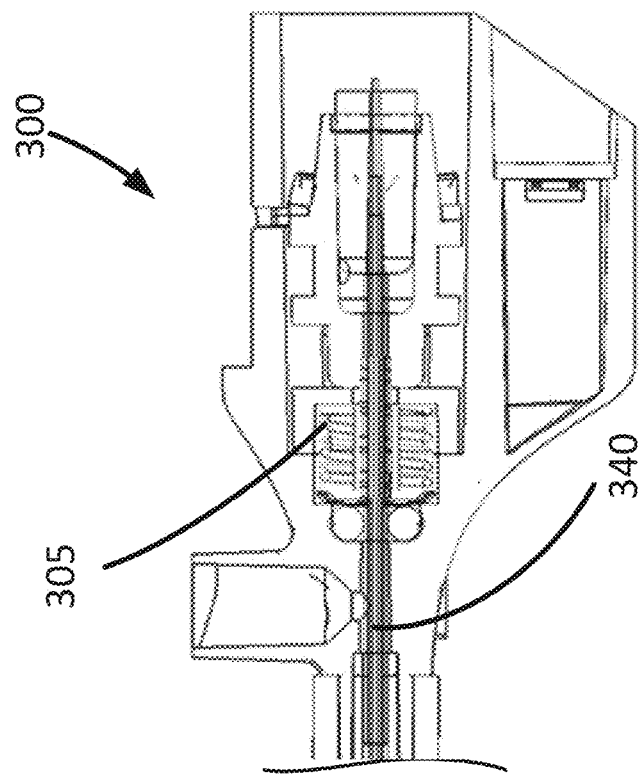
FIG. 3D is a mid-plane cross-sectional view of the proximal hub of the catheter just before being coupled to the catheter drive mechanism.
Figure 3E:
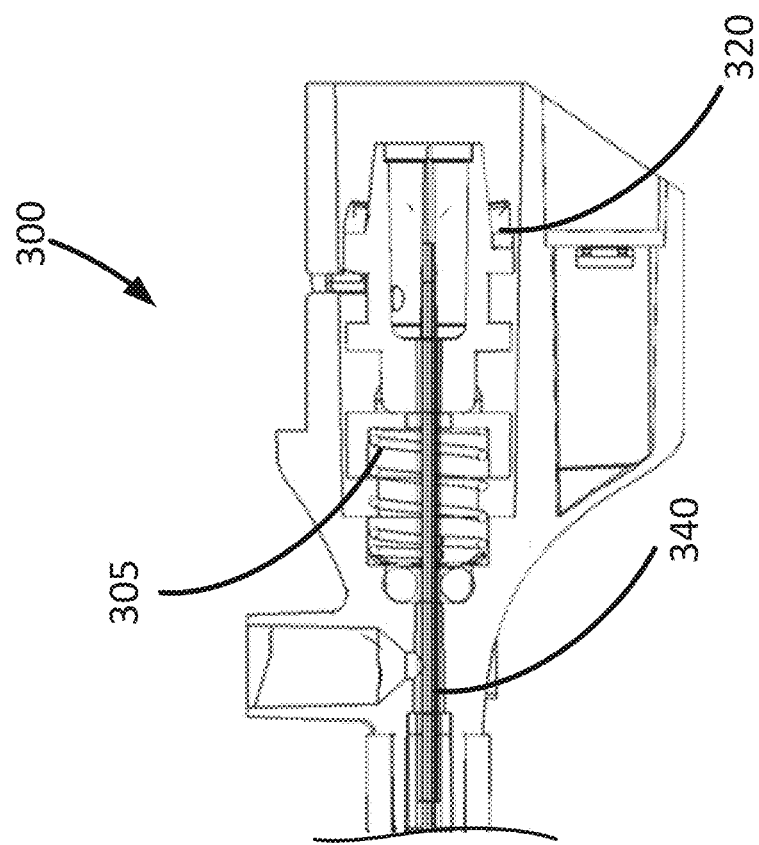
FIG. 3E is a mid-plane cross-sectional view of the proximal hub of the catheter after being coupled to the catheter drive mechanism.

FIGS. 3D and 3E illustrate how coupling can manipulate the axial biasing member 305. FIG. 3D illustrates the position of an axial biasing member 305 when the catheter is not coupled to the catheter drive mechanism. FIG. 3E illustrates the axial biasing member 305 in a compressed position when the catheter is coupled to the catheter drive mechanism and the cable 340 is moved axially. As the catheter is coupled to the catheter drive mechanism, the axial biasing member 305 compresses. The compression of the axial biasing member 305 can bias components of the catheter. The compression of the axial biasing member 305 can forcibly mate the circumferential teeth 320 of the proximal hub 300 of the catheter to the circumferential teeth of the catheter drive mechanism thereby reducing the likelihood of the mated circumferential teeth separating during operation.

Figure 4:
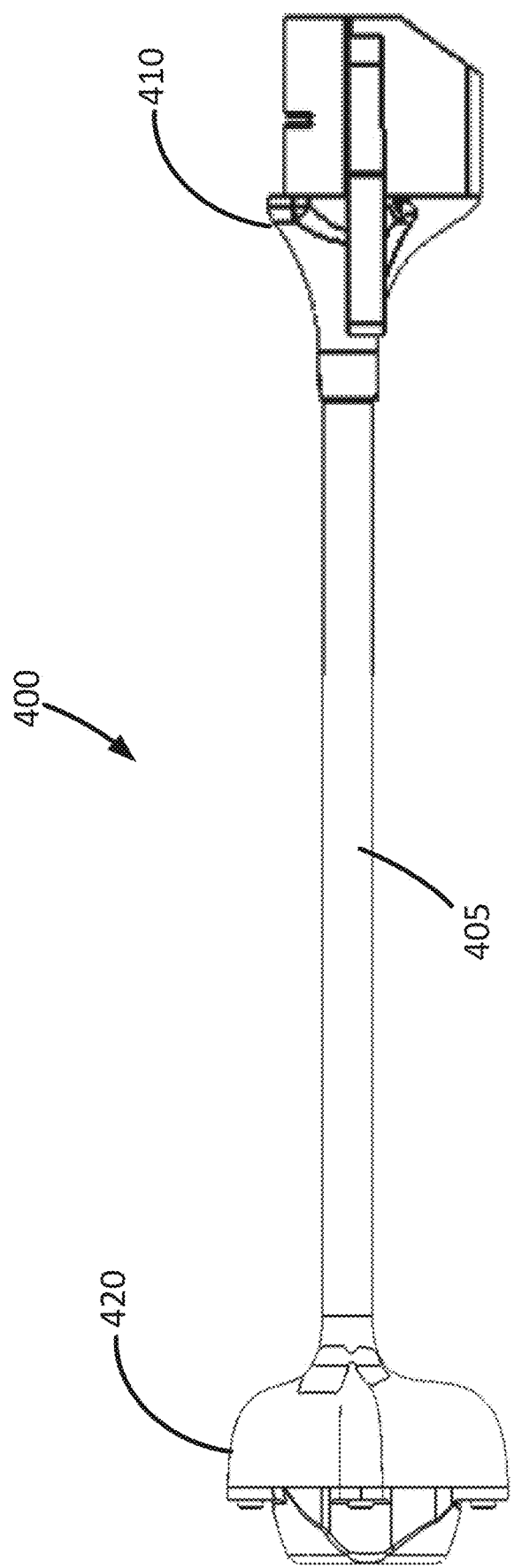
FIG. 4 is a side elevational view of a catheter extension.

FIG. 4 shows a catheter extension 400 that can be used in some intravascular imaging systems. The catheter extension 400 can include an extension body 405, a proximal connector 410, and a distal connector 420. The extension body 405 can have a proximal end. The extension body 405 can have a distal end. The extension body 405 can include a sheath. The sheath can have at least one portion configured to increase the stiffness of the sheath. The sheath can define a lumen. A cable can extend within the lumen. In some embodiments, the sheath can be made with one or more plastics that can provide minimal friction between the cable and sheath.

Figure 5:
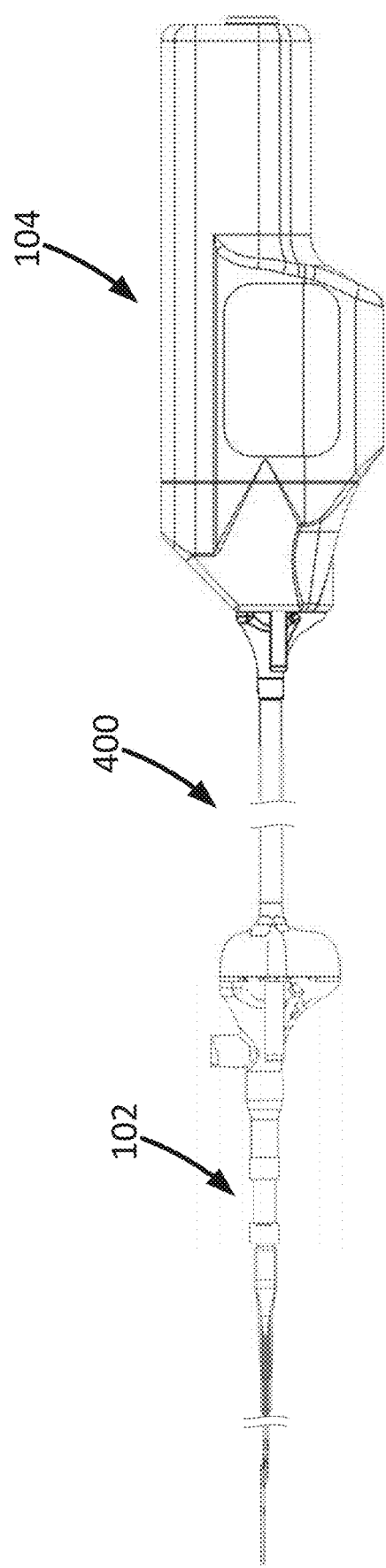
FIG. 5 is a side elevational view of an intravascular imaging system that includes a catheter extension.

The addition of a catheter extension 400 can eliminate the need for a sterile barrier to cover the catheter drive mechanism. An illustrative embodiment of an intravascular imaging system having a catheter extension 400 between the catheter and the catheter drive mechanism and without a sterile barrier over catheter drive mechanism 104 is shown in FIG. 5. The proximal connector 410 of the catheter extension 400 can be coupled to the catheter drive mechanism. The distal connector 420 of the catheter extension 400 can be coupled to the proximal hub of the catheter. The catheter extension 400 can transfer movement between the catheter drive mechanism and the catheter. The catheter extension 400 can have a length of between four feet and six feet. The catheter extension 400 can provide enough distance to reduce the risk of contamination from the non-sterile catheter drive mechanism to the sterile catheter.

The catheter drive mechanism 104 and the catheter extension can be coupled together as illustrated in FIGS. 6A-6E. The proximal connector 410 of the catheter extension can be configured to be mechanically coupled to the catheter drive mechanism 104 using the proximal connector 410 to prevent inadvertent decoupling. Components of the catheter drive mechanism 104 can mate with corresponding components of the proximal connector 410 of the catheter extension. Components of the catheter can mate with corresponding components of the distal connector of the catheter extension. The mating components of the extension catheter, the catheter, and catheter drive mechanism 104 can be configured to rotate components of the catheter by the catheter drive mechanism through the catheter extension after they are coupled. As assembled, the catheter extension can accommodate accumulated tolerance build up within the assembly of the catheter, catheter extension, and catheter drive mechanism 104.

Figure 6A:
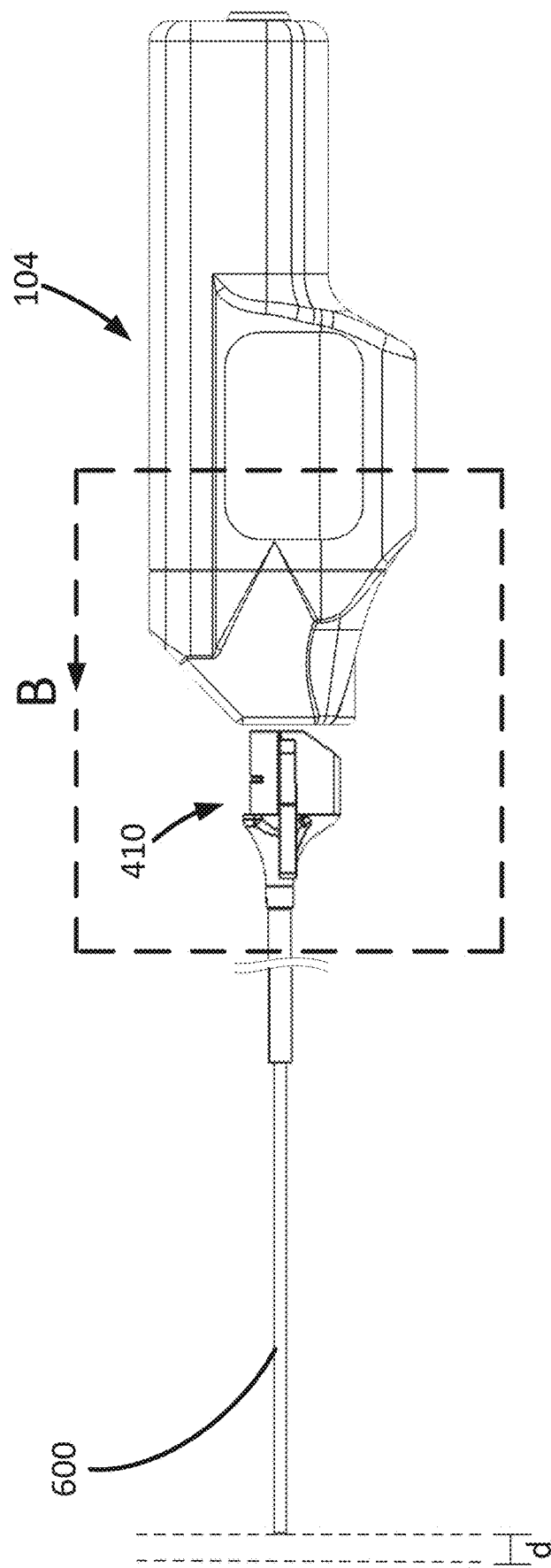
FIG. 6A is a side elevational view of a catheter extension proximal connector just before being coupled to a catheter drive mechanism.

FIG. 6A shows the proximal connector 410 of the catheter extension and the catheter drive mechanism 104 just before being coupled together. The user can press the proximal connector 410 of the catheter extension into the connection port of the catheter drive mechanism 104. The proximal connector 410 of the catheter extension can be configured to mate to the connection port of the catheter drive mechanism. As the catheter extension and the catheter drive mechanism 104 are coupled, components of the catheter extension can become biased in the axial direction. As the proximal connector 410 of the catheter extension is coupled, components of the port can become compressed so as to bias components of the catheter extension.

Figure 6B:
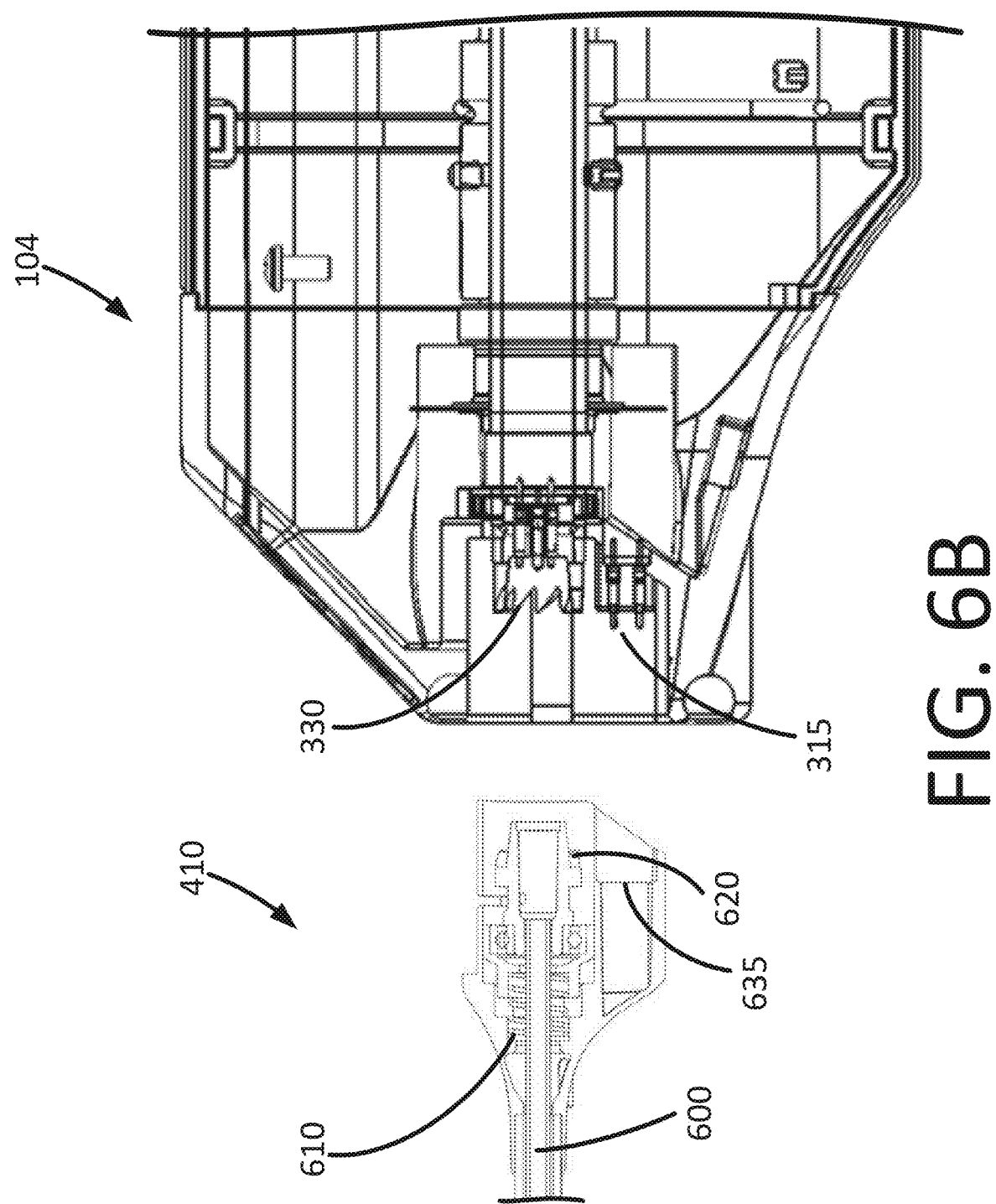
FIG. 6B is a mid-plane cross-sectional view of section B from FIG. 6A.

FIG. 6B shows a cross section of the internal components of an illustrative proximal connector 410 of the catheter before connecting to a catheter drive mechanism. The cable 600 can be configured to be rotated by the catheter drive mechanism 104. The proximal connector 410 can include proximal circumferential teeth 620. The proximal circumferential teeth 620 can be configured to mate with complementary circumferential teeth 330 of the catheter drive mechanism. The proximal circumferential teeth 620 can be configured to be rotated by complementary circumferential teeth 330 of the catheter drive mechanism.

The catheter extension can be constructed to prevent unintentional rotation of the cable. The mating surfaces of the proximal circumferential teeth 620 and the complementary circumferential teeth 330 can be configured to transfer rotation in one direction and discourage rotation in the opposite direction. Further, the cable can be biased in such a way that it can resist rotation of the circumferential teeth in the unintended direction.

Figure 6C:
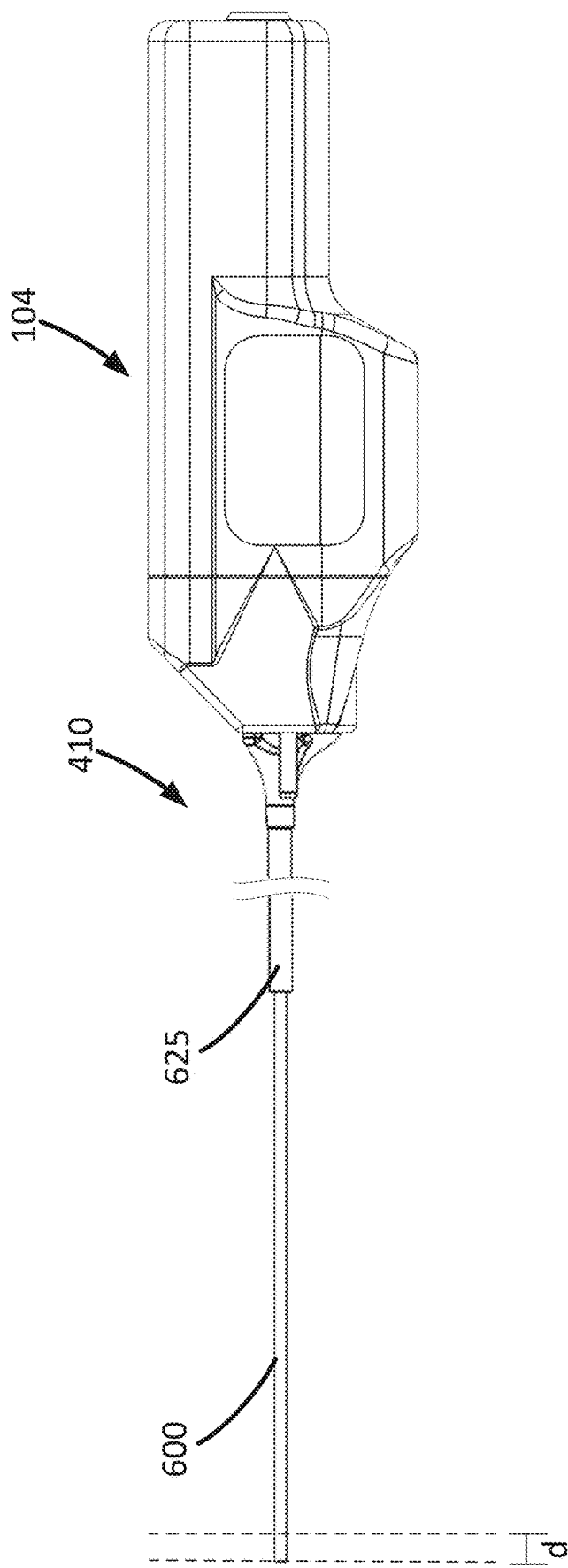
FIG. 6C is a side elevational view of a catheter extension after being coupled to a catheter drive mechanism.

The catheter extension proximal connector 410 and the catheter drive mechanism 104 can be coupled as seen in FIG. 6C. In some embodiments, the proximal connector 410 can resemble the proximal hub of a catheter. The proximal connector 410 can be attached to the sheath 625 at the proximal end of the extension body (405 in FIG. 4). The proximal connector 410 can be configured to be coupled to the catheter drive mechanism 104. In many embodiments, the axial biasing member (610 in FIG. 6B) can be integrated into the proximal connector 410. The proximal connector 410 can include a proximal sealed bearing 630. The proximal connector 410 can be configured to be inserted into a catheter drive port of the catheter drive mechanism 104.

Figure 6E:
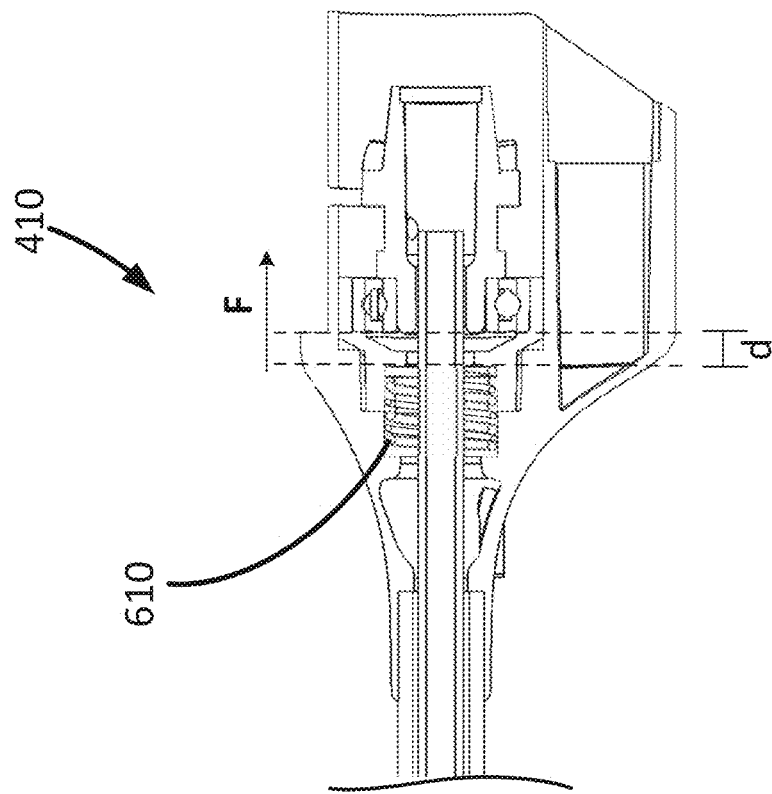
FIG. 6E is a mid-plane cross-sectional view of the proximal connector of the catheter extension after being coupled to the catheter drive mechanism.
Figure 6D:
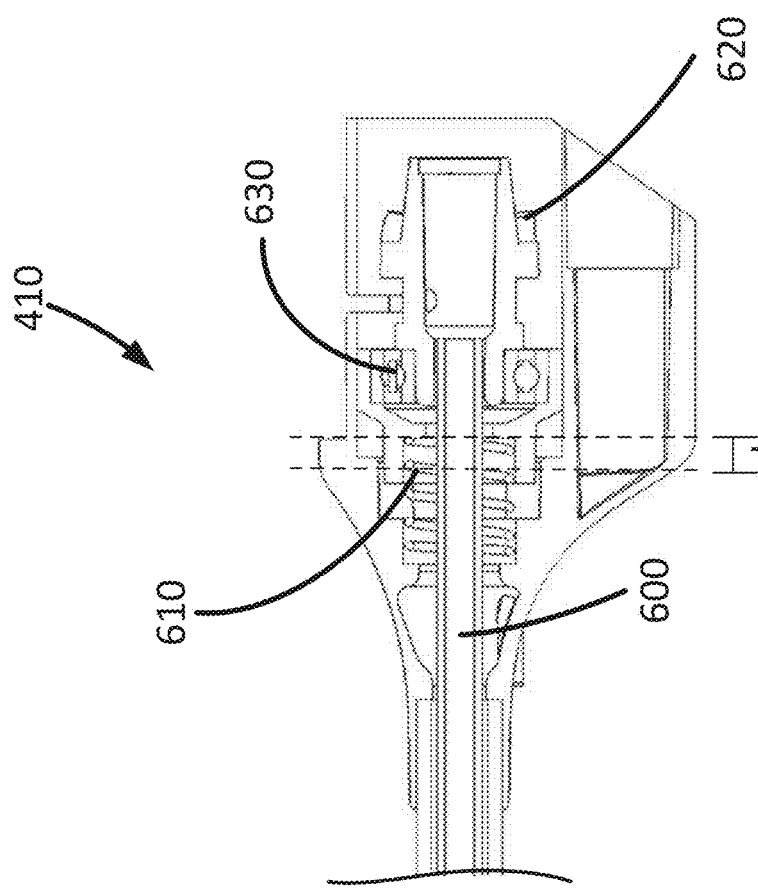
FIG. 6D is a mid-plane cross-sectional view of the proximal connector of the catheter extension just before connecting to the catheter drive mechanism.

As shown in FIGS. 6D and 6E, the position of the cable can be manipulated by the axial biasing member 610 when the proximal connector 410 of the catheter extension is coupled to the catheter drive mechanism. The cable 600 can be configured to communicate electrically with the catheter drive mechanism. The cable 600 can have an impedance of approximately 35Ω. The cable 600 can be configured to provide electrical communication from the catheter drive mechanism to the catheter. The cable 600 can feature braiding and/or multiple layers. The proximal connector 410 of the catheter extension can have at least one electrical connector 635 that corresponds to at least one electrical connector 315 in the catheter drive mechanism.

A system user can use the catheter extension during setup for an operation and during an operation itself to communicate at least safety information and catheter information. The signal between the catheter and catheter drive mechanism can be constant or intermittent and can be transmitted via wired or wireless signals. During setup, the system user can receive information indicating that the catheter extension is coupled to the catheter drive mechanism and/or that the catheter is coupled to the catheter extension. The system user can receive identification information from the catheter. These portions of information can help minimize operation risks by ensuring proper setup before conducting an operation. The system can also be configured to transfer signals from, for instance, a transducer connected to the catheter for use by the system user. For example, the transferred signal can be sent to a read out device and other system components for imaging or communicating positional information and/or for calibration or to make adjustments during an operation.

In some embodiments, the proximal connector 410 can transfer the movement of the catheter drive mechanism at the proximal end of the catheter extension. The catheter extension 400 can include an axial biasing member 610. The proximal connector 410 of the catheter extension can have an axial biasing member seat. The axial biasing member 610 can rest against the axial biasing member seat in the proximal connector 410 of the catheter. The axial biasing member 610 can be connected to the proximal circumferential teeth 620. The axial biasing member 610 can be an elastic object such as a mechanical device (e.g. a spring) or a sleeve (e.g. an accordion connector or adapter). When the catheter extension proximal connector 410 is coupled to the catheter drive mechanism, the axial biasing member 610 can be compressed, thereby exerting a force on components of the proximal connector 410 in the opposite direction of the compression. The axial biasing member 610 can be made of variable resistance, folds, stiffness, or material.

FIG. 6E illustrates the axial biasing member 610 in a compressed position when the proximal connector 410 of the catheter extension is coupled to the catheter drive mechanism and the cable 600 is moved axially. The axial biasing member 610 can be coupled to the cable 600. The axial biasing member 610 can be configured to exert a force on the cable 600 in a first axial direction F. Force exerted on the cable 600 in the first axial direction F can facilitate connection between the cable 600 and the catheter drive mechanism. Force exerted on the cable 600 in the first axial direction F can permit movement of the cable 600 in a second axial direction. The second axial direction can be opposite of the first axial direction.

Figure 7A:
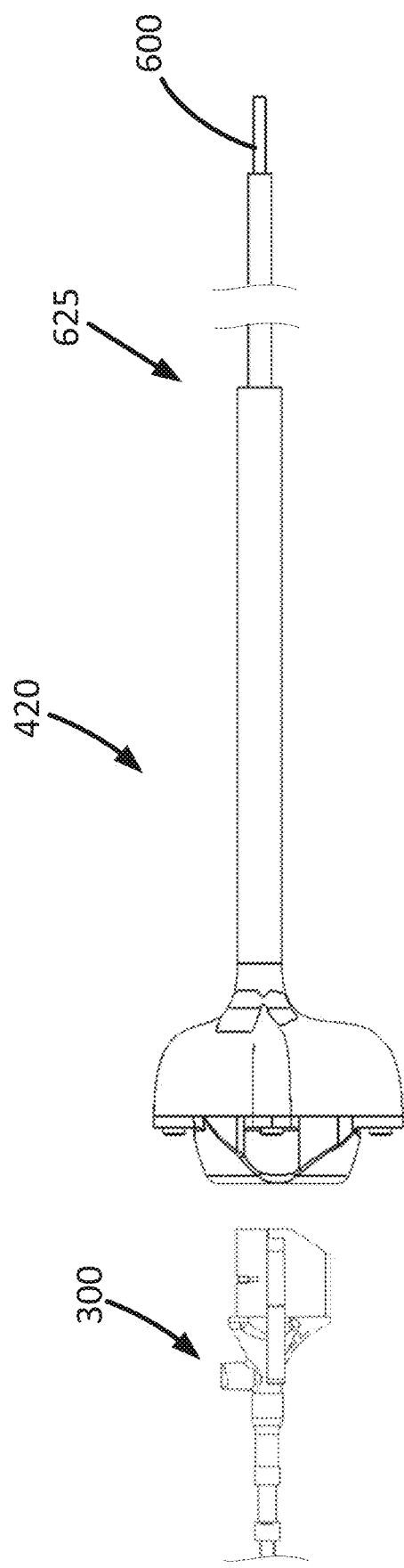
FIG. 7A is a side elevation view of the proximal hub of the catheter just before being coupled to the distal connector of the catheter extension.
Figure 7B:
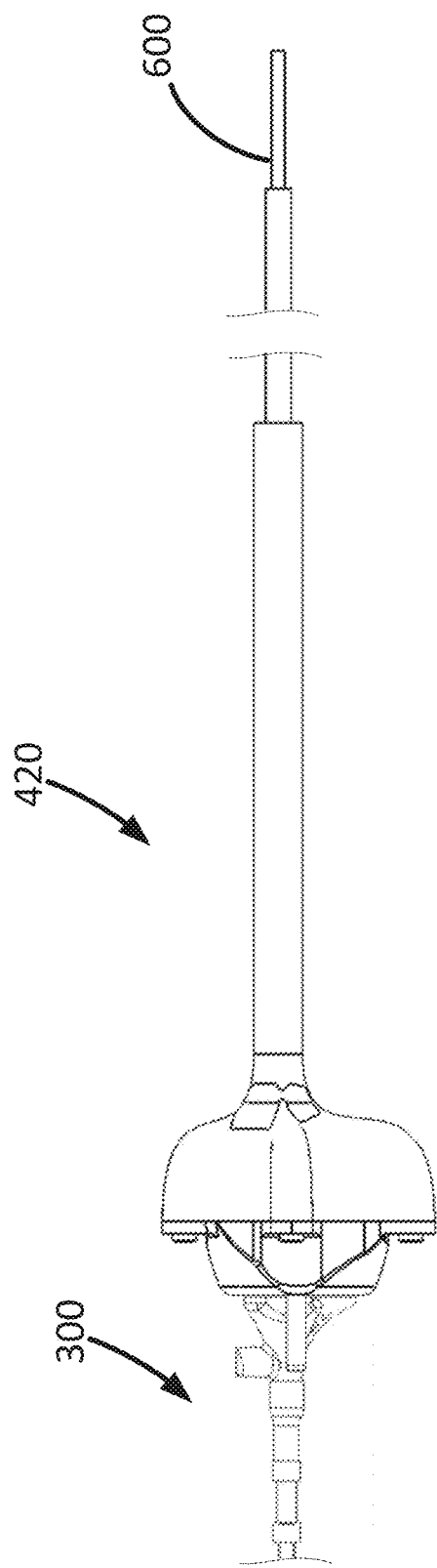
FIG. 7B is a side elevation view of the proximal hub of the catheter after being coupled to the distal connector of the catheter extension.

FIGS. 7A and 7B show the catheter extension distal connector 420 and a proximal hub 300 of a catheter. As shown, the distal connector 420 of the catheter extension can be coupled to the proximal hub 300 of the catheter similar to how the proximal hub 300 would be coupled to a catheter drive mechanism. The distal connector 420 can be attached to the sheath 625 at the distal end of the extension body (405 in FIG. 4). The distal connector 420 can be configured to be coupled to the catheter.

The catheter extension distal connector 420 can incorporate several components to accommodate the catheter. The distal connector 420 can have a connection port. The connection port can be configured to receive the proximal hub 300 of the catheter. The distal connector 420 can have an electrical switch configured to allow for transmission of an electrical control signal between the catheter and the catheter drive mechanism. In some embodiments, the axial biasing member can be integrated into the distal connector 420. The distal connector 420 can include a distal sealed bearing 740.

The cable can be configured so as to minimize additional mechanical load to the catheter drive mechanism. The cable can be connected to at least one bearing in the proximal connector and distal connector of the catheter extension. The bearings can be ball or roller bearings. The bearing(s) can reduce the amount of friction resulting from rotating components in the catheter extension, thereby reducing additional mechanical load to the catheter drive mechanism. This can allow the catheter extension to be used with existing catheter drive mechanisms without having to make significant modifications to the catheter drive mechanism.

The coupling between the catheter extension distal connector 420 and the catheter can mimic the coupling between the catheter drive mechanism and the catheter. The user can press the proximal hub 300 of the catheter into the distal connector 420 of the catheter extension. The catheter extension distal connector 420 and the catheter can have corresponding mating surfaces. The catheter extension distal connector 420 can have one or more electrical connections that mate with corresponding electrical connections in the proximal hub 300. The electrical connections can allow for electrical transfer between the catheter and the catheter drive mechanism.

FIG. 7B shows the catheter extension distal connector 420 and the proximal hub 300 when coupled together. At this point, the circumferential teeth of the proximal hub 300 can be mated to the catheter drive mechanism such that the catheter drive mechanism can rotate components of the catheter. The electrical connections can be connected to provide electrical transfer after the catheter and the catheter drive mechanism are coupled. The catheter extension distal connector 420 and the proximal hub 300 can be mechanically coupled together to prevent inadvertent decoupling.

The extension body can be configured to facilitate electrical communication between the proximal connector and distal connector 420. For example, an electrical signal can pass between the mating electrical connections between the proximal connector and catheter drive mechanism, between the catheter extension, and between electrical connections between the catheter proximal hub and distal connector 420. The cable 600 can be made from a variety of conductive materials. The cable 600 can feature a coaxial communication cable made of a conductive material. A communication cable can, for instance, be positioned exterior to the cable 600 and run through the sheath of the extension body. The cable 600 and communication cable can be connected to the electrical connectors in the proximal connector and the distal connector 420.

Figure 7C:
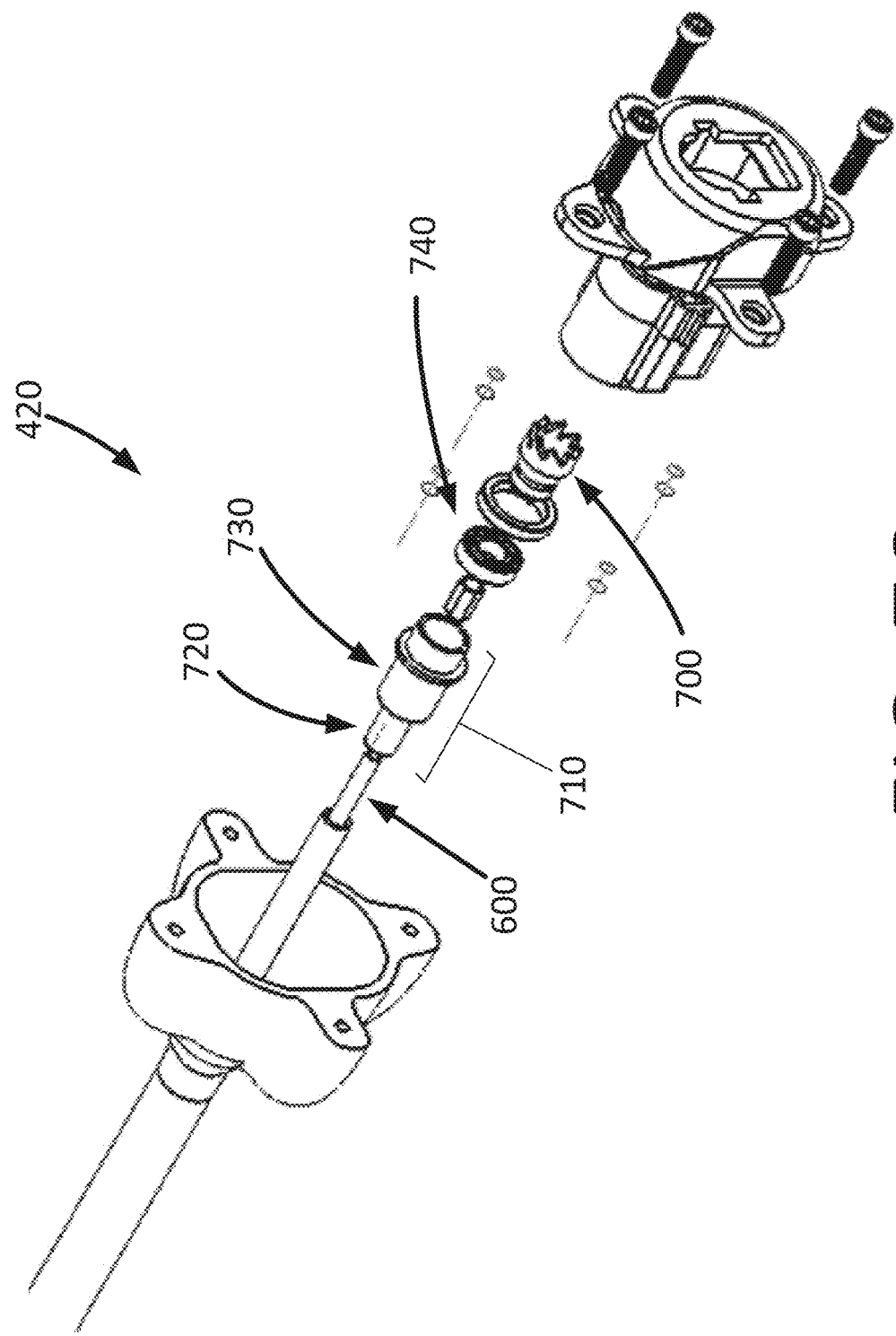
FIG. 7C is an exploded view of the distal connector of the catheter extension.

In some embodiments, movement of the catheter drive mechanism can be transferred through the catheter extension to the catheter. For example, referring to FIG. 7C, the cable 600 can be configured to rotate a cable of the catheter. The distal connector 420 can include distal circumferential teeth 700. The distal circumferential teeth 700 of the distal connector 420 can be configured to mate with complementary teeth of the catheter. The distal circumferential teeth 700 of the distal connector 420 can be configured to mate with and rotate complementary teeth of the catheter.

Illustrative embodiments of the catheter extension can have an axial key 710 to accommodate tolerance stack up. The axial key 710 can be coupled to the cable 600. The axial key 710 can include a tab 720 and a slot 730. The axial key tab 720 can have an outer profile. The slot 730 can have an inner profile. The inner profile of the slot 730 can be a variety of shapes (e.g., quadrilateral, hexagonal, octagonal, etc.). The outer profile of the tab 720 can be a variety of shapes (e.g., quadrilateral, hexagonal, octagonal, etc.). The inner profile of the slot 730 can complement the outer profile of the tab 720.

In some embodiments, the tab 720 can be attached to, and movable with, the cable 600. In some such embodiments, the slot 730 can be fixed relative to the tab 720 such that the tab 720 can move axially within the slot 730 as the cable 600 moves axially. The slot 730 can permit the tab 720 to move in the second axial direction within the slot 730. The slot 730 can be coupled to the distal circumferential teeth 700. The axial key 710 can be integrated into the distal connector 420. The axial key 710 can cause the distal circumferential teeth 700 and the cable 600 to rotate together.

In some embodiments, the distal connector 420 can be configured to not rotate when the catheter extension proximal connector is not coupled to the catheter drive mechanism. The axial key tab can be in contact with the slot when the catheter extension proximal connector is coupled to the catheter drive mechanism. The axial key tab may not be in contact with the slot when the catheter extension proximal connector is not coupled to the catheter drive mechanism.

The axial key can be of a length that is proportional to the amount of axial bias in the catheter extension from the axial biasing member as shown in FIGS. 6A and 6C-6E. The axial key can be in an axial position proportional to the amount of axial bias in the catheter extension from the axial biasing member 610. For example, during assembly, when the proximal connector 410 is coupled to the catheter drive mechanism 104, the axial biasing member 610 can become compressed a distance d as seen in FIGS. 6D and 6E. The cable 600 can then be axially displaced a distance proportional to the distance d as shown in FIGS. 6A and 6C.

Referring again to FIG. 7C, the axial key 710 can enable the distal connector port (800 in FIG. 8A) to have a fixed depth. As the cable 600 moves distally in the axial direction, the tab 720 can likewise move distally in the axial direction within the slot 730. The distance of the axial movement can be proportional to (e.g., the same as) the distance that the connection of the proximal connector to the catheter drive mechanism causes the cable 600 to move. In many embodiments, the slot 730 can be configured such that the tab 720 is within the slot 730 both when the cable 600 is in its most proximal position and when the cable 600 is in its most distal position. In this way, operational connection between the cable 600 and the distal circumferential teeth 700 can be maintained irrespective of axial movement of the cable 600. Thus, the connector port (800 in FIG. 8A) of the distal connector 420 can present the same kind of catheter interface as the catheter drive mechanism.

As shown in FIGS. 8A and 8B, in some embodiments, the distal connector 420 of the catheter extension can resemble the catheter drive mechanism 104. The distal connector 420 can include a port 800 configured to receive a proximal hub of the catheter. The port 800 can have a structural configuration that mimics that of the catheter drive port 810. As the proximal hub of the catheter is inserted into the distal connector port 800, the catheter and the catheter extension can become mechanically coupled together. The distal connector 420 can also have an electrical switch that can allow for transmission of an electrical control signal.

In some embodiments, the axial biasing member can be integrated into the distal connector 420 of the catheter extension, and the axial key can be integrated into the proximal connector of the catheter extension. In this configuration, the combination of the axial biasing member and the axial key can operate similarly to embodiments described herein, for example, when the axial biasing member is in the proximal connector and the axial key is integrated into the catheter extension distal connector. The catheter drive mechanism can rotate the cable by rotating mating components of the catheter drive mechanism and the catheter extension proximal connector. The axial key tab can be connected to the cable. The axial slot can be included in the proximal connector of the catheter extension and configured to receive and be rotated by the axial key tab without translating axial movement of the cable. Rotation of the axial key can rotate mating components of the catheter and the catheter extension distal connector.

Figure 9:
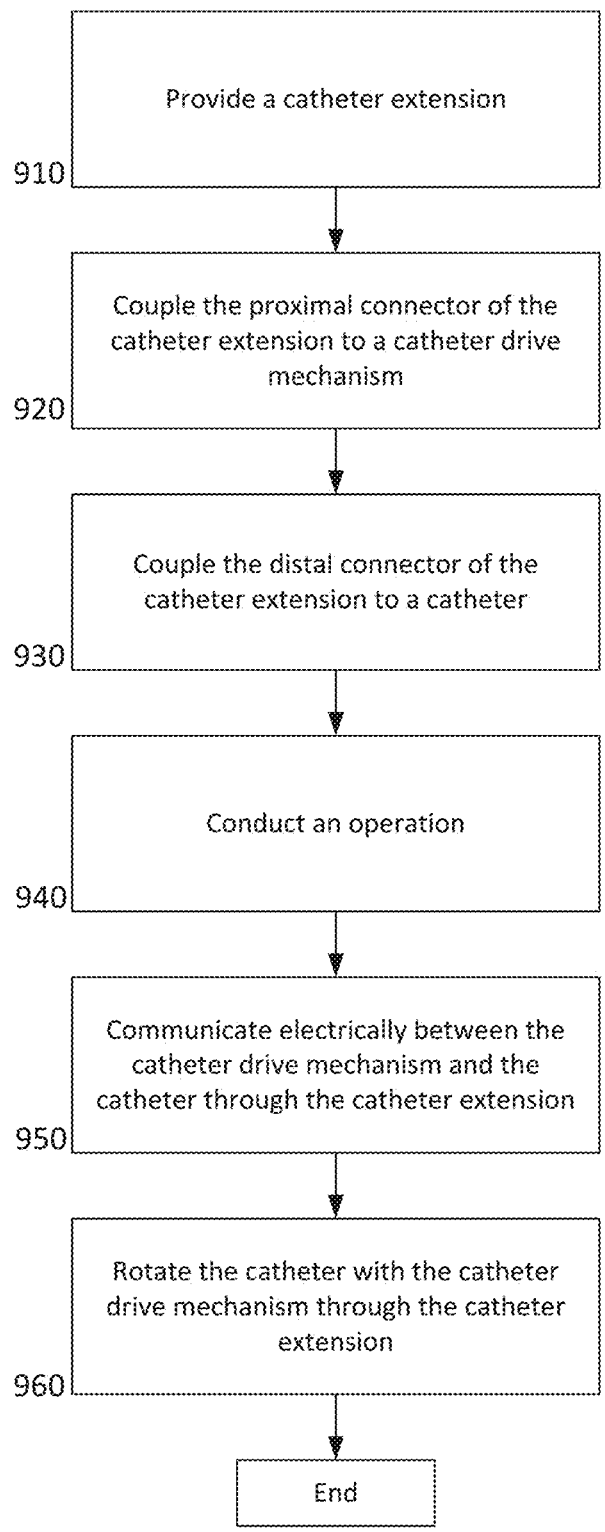
FIG. 9 is a flow diagram of an illustrative method for using a catheter extension.

FIG. 9 is a diagram for a method of extending a catheter assembly. The method can include providing a catheter extension 910 such as those discussed elsewhere herein. The method can include coupling the proximal connector of the catheter extension to a catheter drive mechanism 920. The method can include coupling the distal connector of the catheter extension to a catheter 930.

Coupling in some illustrative methods can move components of the catheter extension. The coupling can cause the axial biasing member to exert a force on the cable in a first axial direction to facilitate connection between the cable and either the catheter drive mechanism or the catheter. The coupling can permit movement of the cable in a second axial direction. The second axial direction can be opposite of the first axial direction. The coupling can permit the tab to move in the second axial direction within the slot 960.

The illustrative method can be sterilely used during operations. The method can further include conducting an operation 940. The method can include conducting an operation without covering the catheter drive mechanism with a sterile barrier. The operation can involve communicating electrically between the catheter drive mechanism and the catheter through the catheter extension 950. The operation can involve rotating the catheter with the catheter drive mechanism through the catheter extension 960. The operation can include intravascular ultrasound.

In some embodiments, the catheter can facilitate communicating catheter information. The method can further include providing catheter information to the catheter drive mechanism through an electrical signal pathway in the catheter extension. The catheter information can include one or more components. The catheter information can include that the catheter extension is coupled to the catheter drive mechanism. The catheter information can include that the catheter extension is coupled to the catheter drive mechanism. The catheter information can include that the catheter is coupled to the catheter extension. The catheter information can include identification information from the catheter.

Various examples have been described with reference to certain disclosed embodiments. The embodiments are presented for purposes of illustration and not limitation. One skilled in the art will appreciate that various changes, adaptations, and modifications can be made without departing from the scope of the invention.

What is claimed is:

1. A catheter extension comprising:
    (a) an extension body having a proximal end and a distal end, the extension body including a sheath defining a lumen and a cable extending within the lumen;
    (b) a proximal connector attached to the sheath at the proximal end of the extension body, the proximal connector being configured to be coupled to a catheter drive mechanism;
    (c) a distal connector attached to the sheath at the distal end of the extension body, the distal connector being configured to be coupled to a catheter;
    (d) an axial biasing member coupled to the cable and integrated into either the proximal connector or the distal connector, the axial biasing member being configured to (i) exert a force on the cable in a first axial direction to facilitate connection between the cable and either the catheter drive mechanism or the catheter and (ii) permit movement of the cable in a second axial direction, the second axial direction being opposite of the first axial direction; and
    (e) an axial key coupled to the cable and integrated into whichever of the proximal connector and the distal connector is not coupled to the axial biasing member, the axial key including (i) a tab attached to the cable and having an outer profile and (ii) a slot with an inner profile that complements the outer profile of the tab, the slot permitting the tab to move in the second axial direction within the slot;
    wherein the proximal connector includes proximal circumferential teeth configured to mate with and be rotated by complementary teeth of the catheter drive mechanism, and wherein the distal connector includes distal circumferential teeth configured to mate with and rotate complementary teeth of the catheter, and wherein the proximal circumferential teeth and the complementary teeth of the catheter drive mechanism have mating surfaces configured to transfer rotation from the catheter drive mechanism to the cable in one direction and discourage rotation in an opposite direction.

2. The catheter extension of claim 1, wherein the cable is configured to provide electrical communication from the catheter drive mechanism to the catheter.

3. The catheter extension of claim 1, wherein the cable is configured to be rotated by the catheter drive mechanism and to rotate a cable of the catheter.

4. The catheter extension of claim 1, wherein the slot is coupled to the distal circumferential teeth and the axial key causes the distal circumferential teeth and the cable to rotate together.

5. The catheter extension of claim 1, wherein the proximal connector comprises a proximal sealed bearing and the distal connector comprises a distal sealed bearing.

6. The catheter extension of claim 1, wherein the catheter drive mechanism comprises a patient interface module.

7. The catheter extension of claim 1, wherein the axial biasing member is integrated into the proximal connector and the axial key is integrated into the distal connector.

8. The catheter extension of claim 1, wherein the inner profile of the slot and the outer profile of the tab are hexagonal.

9. The catheter extension of claim 1, wherein the proximal connector is configured to be inserted into a catheter drive port of the catheter drive mechanism, and wherein the distal connector includes a port configured to receive a proximal hub of the catheter, the port having a structural configuration mimicking that of the catheter drive port.

10. The catheter extension of claim 1, wherein the cable has an impedance of 35 Ω.

11. The catheter extension of claim 1, wherein the catheter extension has a length of between four feet and six feet.

12. A method comprising:
    (a) providing a catheter extension, the catheter extension comprising:
        (i) an extension body having a proximal end and a distal end, the extension body including a sheath defining a lumen and a cable extending within the lumen;
        (ii) a proximal connector attached to the sheath at the proximal end of the extension body;
        (iii) a distal connector attached to the sheath at the distal end of the extension body;
        (iv) an axial biasing member coupled to the cable and integrated into either the proximal connector or the distal connector; and
        (v) an axial key coupled to the cable and integrated into whichever of the proximal connector and the distal connector is not coupled to the axial biasing member, the axial key including (A) a tab attached to the cable and having an outer profile and (B) a slot with an inner profile that complements the outer profile of the tab; and
    (b) coupling (i) the proximal connector of the catheter extension to a catheter drive mechanism and (ii) the distal connector of the catheter extension to a catheter, wherein the coupling causes the axial biasing member to (A) exert a force on the cable in a first axial direction to facilitate connection between the cable and either the catheter drive mechanism or the catheter and (B) permit movement of the cable in a second axial direction, the second axial direction being opposite of the first axial direction, and wherein the coupling permits the tab to move in the second axial direction within the slot;
    wherein the proximal connector includes proximal circumferential teeth configured to mate with and be rotated by complementary teeth of the catheter drive mechanism, and wherein the distal connector includes distal circumferential teeth configured to mate with and rotate complementary teeth of the catheter, and wherein the proximal circumferential teeth and the complementary teeth of the catheter drive mechanism have mating surfaces configured to transfer rotation from the catheter drive mechanism to the cable in one direction and discourage rotation in an opposite direction.

13. The method of claim 12, wherein the axial biasing member is integrated into the proximal connector and the axial key is integrated into the distal connector.

14. The method of claim 12, further comprising:
(c) conducting an operation involving (i) communicating electrically between the catheter drive mechanism and the catheter through the catheter extension and (ii) rotating the catheter with the catheter drive mechanism through the catheter extension.

15. The method of claim 12, further comprising:
(c) conducting an intravascular ultrasound procedure without covering the catheter drive mechanism with a sterile barrier.

16. The method of claim 12, further comprising:
(c) providing catheter information to the catheter drive mechanism through an electrical signal pathway in the catheter extension.

17. The method of claim 16, wherein the catheter information includes one or more of (i) that the catheter extension is coupled to the catheter drive mechanism, (ii) that the catheter is coupled to the catheter extension, and (iii) identification information from the catheter.

* * * * *